US007208153B2

(12) United States Patent
Müller et al.

(10) Patent No.: US 7,208,153 B2
(45) Date of Patent: Apr. 24, 2007

(54) METHOD FOR THE IMPROVEMENT OF NEURONAL REGENERATION

(75) Inventors: Hans Werner Müller, Dusseldorf (DE); Christine C. Stichel-Gunkel, Dusseldorf (DE)

(73) Assignee: Neuraxo Biopharmaceuticals GmbH, Erkrath (DE)

( * ) Notice: Subject to any disclaimer, the term of this patent is extended or adjusted under 35 U.S.C. 154(b) by 406 days.

(21) Appl. No.: 10/837,762

(22) Filed: May 4, 2004

(65) Prior Publication Data

US 2005/0118177 A1 Jun. 2, 2005

Related U.S. Application Data

(63) Continuation of application No. 09/423,622, filed as application No. PCT/EP98/02808 on May 13, 1998, now abandoned.

(30) Foreign Application Priority Data

May 14, 1997 (EP) .................................. 97107846

(51) Int. Cl.
*A61K 39/395* (2006.01)
*A61K 38/16* (2006.01)
*A61K 31/444* (2006.01)

(52) U.S. Cl. ......................... 424/145.1; 514/6; 514/331

(58) Field of Classification Search ..................... None
See application file for complete search history.

(56) References Cited

U.S. PATENT DOCUMENTS

| 4,457,936 A | 7/1984 | Draeger et al. |
| 4,717,727 A | 1/1988 | Günzler et al. |

FOREIGN PATENT DOCUMENTS

| WO | 83/04104 | 11/1983 |
| WO | 93/19783 | 10/1993 |
| WO | 94/17831 | 8/1994 |
| WO | WO 94/17831 | 8/1994 |
| WO | 95/10305 | 4/1995 |
| WO | WO 95/10305 | 4/1995 |
| WO | 95/13291 | 5/1995 |
| WO | WO 95/13291 | 5/1995 |
| WO | 96/00582 | 1/1996 |

OTHER PUBLICATIONS

Pettit et al. The development of site specific drug-delivery systems for protein and peptide biopharmaceuticals. Trends in Biotech 16: 343-349, 1998.*
Hermanns et al. 2,2'-bipyridine but not its dicarboxylic acid derivative fails to prevent collagen scar formation after spinal cord injury in the adult rat. Society for Neurosci Abs 26(1-2): 3236, 2000.*
Joosten et al. Collagen IV deposits do not prevent regrowing axons from penetrating the lesion site in spianl cord injury. J Neurosci Res 62: 686-691, 2000.*
Stichel et al. Basal membrane-depleted scar in lesioned CNS: characteristics and relationships with regenerating axons. Neurosci 93(1): 321-333, 1999.*
Feringa et al. 1980. Basal lamina formation at the site of spinal cord transection. Ann Neurol 8: 148-154.*
White and Kraus. 1993. Brain injury and repair machanisms: the potential for pharmacologic therapy in closed-head trauma. Ann Emergency Medicine 22(6): 632-646.*
Stichel and Muller. 1995. Regenerative failure in the mammalian CNS. Trends in Neurosciences 18(3): 128-129.*
Jackowski. 1995. Neural injury repair: hope for the future as barriers to effective CNS regeneration become clearer. British J. of Neurosurgery 9: 303-317.*
Kruczewski et al. 1992. Glial response to transection of the rat postcommissural fornix. European J. Neurosciences S5: 190.*
Feringa et al., "Basal Lamina Formation at the Site of Spinal Cord Transection", Annals of Neurology, vol. 8, (1980), 148-154.
Franklin et al., "Approaches to the design of anti-fibrotic drugs", Biochemical Society Transactions, vol. 19, (1991).
Cunliffe et al., "Novel Inhibitors of Proly 4-Hydroxylase. 3.[1] Inhibition by the Substrate Analogy—Oxaloglycine and its Derivatives", J. Med. Chem., 35, (1992), 2652-2658.
Dowell, Robert I. and Hadley, Elizabeth M., "Novel Inhibitors of Prolyl 4-Hydroxylase", J. Med. Chem., 35, (1992), 800-804.
Hales, Neil J. and Beattie, John F., "Novel Inhibitors of Prolyl 4-Hydroxylase. 5.[1] The Intriguing Structure-Activity Relationships Seen with 2,2'-Bipyridine and its 5,5'-Dicarboxylic Acid Derivatives", J. Med. Chem., 36, (1993), 3853-3858.
Hunt et al., "The Effect of Desferrioxamine on Fibroblasts and Collagen Formation in Cell Cultures," British Journal of Haematology, 41, (1979), 69-76.
Ishimaru et al., Inhibition of Prolyl Hydroxylase Activity and Collagen Biosynthesis by Fibrostatin C, AS novel Inhibitor Produced by *Streptomyces catenulae* Subsp. *Griseospora* No. 23924, The Journal of Antibiotics, vol., XLI, (1988), 1668-1674.
Sasaki et al., Reduction of Collagen Production in Keloid Fibroblast Cultures by Ethyl-3-,4-dihydroxybenzoate, The Journal of Biological Chemistry, 262, (1987), 9397-9403.
Puchala, Elizabeth and Windle, William F., "The Possibility of Structural and Functional Restitution after Spinal Cord Injury. A Review", Experimental Neurology, 55, (1977), 1-42.
Franklin, Trevor J. and Hitchen, Michael, "Inhibition of collagen hydroxylation by 2,7, 8-trihydroxyanthraquinone in embryonic-chick tendon cells", Biochem J., 261, (1989), 127-130.

(Continued)

*Primary Examiner*—Janet L. Andres
*Assistant Examiner*—Gregory Emch
(74) *Attorney, Agent, or Firm*—Jacobson Holman PLLC

(57) ABSTRACT

A method for the improvement of neuronal regeneration by prevention or inhibition of basal membrane formation induced by a lesion of neuronal tissue.

16 Claims, 4 Drawing Sheets

OTHER PUBLICATIONS

Figure 1:
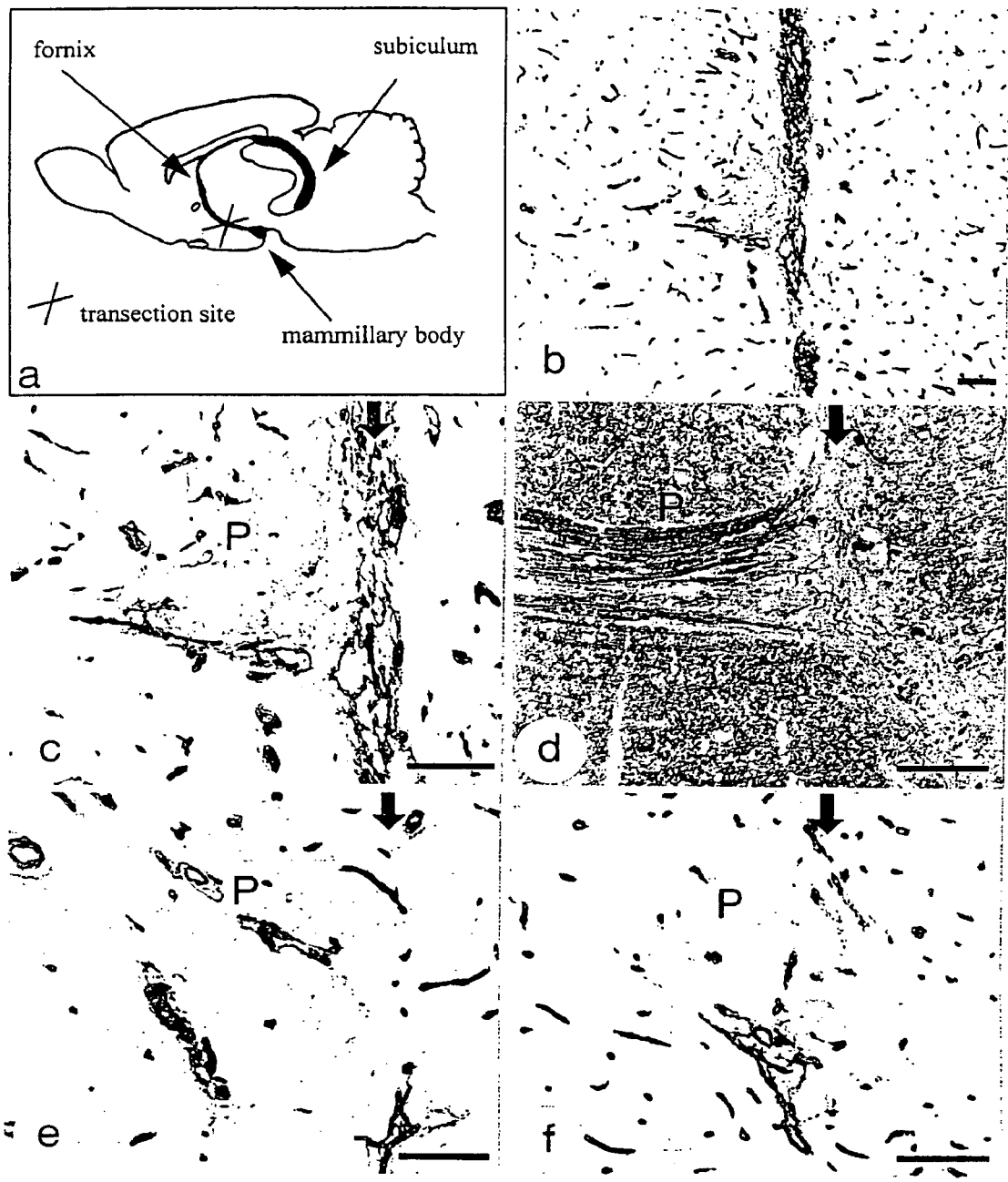

Gunzler et al., "Time-dependent inactivation of chick-embryo prolyl 4-hydroxylase by coumalic acid", Biochem. J. 242, (1987), 163-169.

Karvonen et al., "Specific Inactivation of Prolyl 4-Hydroxylase and Inhibition of Colleagen Synthesis by by Oxaproline-containing Peptides in Cultured Human Skin Fibroblasts", The Journal of Biological Chemistry, 265, (1990), 8415-8419.

Einheber et al., "Transforming Growth Factor-β1 Regulates Axon/Schwann Cell Interactions", The Journal of Cell Biology, 129, (1993), 443-458.

Stichel, C.C. and Muller, H.W., Relationship between injury-induced astrogliosis, laminin expression and axonal sprouting in the adult rat brain, Journal of Neurocytology, 23, (1994), 615-630.

Müller et al., "Astroglial Neurotrophic and neurite-promoting factors," Pharmacology & Therapeutics, 65, (1995) 1-18.

* cited by examiner

METHOD FOR THE IMPROVEMENT OF NEURONAL REGENERATION

This application is a continuation of U.S. patent application Ser. No. 09/423,622, filed Feb. 8, 2000, now abandoned, which is the national stage entry of PCT/EP98/02808, filed May 13, 1998, which claims priority to European Patent application no. 97107846.4, filed May 14, 1997.

The present invention refers to a method for the improvement of neuronal regeneration, a medicament for the improvement of neuronal regeneration and use of a specific inhibitor substance.

Injury to adult mammalian CNS fiber tracts leads to the formation of a lesion scar consisting of a convoluted fringe of astroglial processes lined by a basal membrane (BM). This lesion scar is implicated as a major extrinsic constraint to effective axon regeneration in brain and spinal cord (1–4). While the dense astrocytic network is a.,permissive substrate for axon growth (5, 6), the presence of BM has-been hypothesized as a crucial impediment for regeneration (7). However, experimental evidence was not shown. To the contrary, when the BM formed after a lesion of neuronal tissue was removed (24), no improved regeneration could be reproducibly monitored (25). Therefore, it is still of great importance to have a method for improving regeneration of injured neurons.

WO 93/19783 discloses a method for preventing, suppressing or treating a CNS pathology characterized by a deleterious accumulation of extracellular matrix in a tissue by contacting the tissue with an agent that inhibits the extracellular matrix producing activity of TGF-β. The disclosed methods can be used to prevent, suppress or treat scar formation in the CNS. As useful agents there are neutralizing anti-TGF-β antibodies, Arg-Gly-Asp-containing peptides, decorin and its functional equivalence such as biglycan and TGF-β antagonists. TGF-β has a wide spectrum of physiological functions such as activation of cell of the immune system, inhibition of cell proliferation, neurotrophic effects on sensory neurons, inhibition of Schwann cell myelination, anti-profilerative effects on glial cells, immunsuppressive effects, stimulation of extracellular matrix deposition and chemoattraction of microglia cells. The anti-TGF-β treatment would induce the opposite effects. Inhibition of TGF-β activity leads to numerous non-specific cellular responses, which may even lead to unwanted side effects. One object of the invention is to avoid such potential unwanted side effects.

Surprisingly, improvement of regeneration of neuronal tissue after lesion is achieved by a method of the present invention.

According to the method of the invention improved regeneration of injured neuronal tissue is achieved by specific prevention or specific inhibition of-basal membrane formation induced by a lesion of neuronal tissue.

The basal membrane is a structure which is composed of different elements. Elements of the basal membrane are collagen IV, laminin, entactin (Nidogen) accessory substances. The assembly of the elements to the basal membrane is performed by enzymes which may be assisted by cofactors.

Inhibitors of TGF-β are not involved with a specific prevention or specific inhibition of basal membrane formation induced by lesion of neuronal tissue. According to the present invention it is achieved in an advantageous manner that a specific interaction is provided.

Preferably, the formation of the basal membrane is prevented or inhibited by applying a specific inhibitor substance of the synthesis of basal membrane building elements, or the assembly of basal membrane building elements, or both the synthesis of basal membrane building elements and the assembly of basal membrane building elements to a body in need thereof. The building elements of the basal membrane are in particular those which are involved with the formation of the basal membrane, for instance molecular structures building up the basal membrane, such as monomeric compounds, accessory substances, substances for the assembly of the components of the basal membrane and the like.

In particular, the basal membrane building elements are selected from the group consisting of collagen IV, laminin, entactin, accessory substances for proper function, or the assembly of the basal membrane, or both the proper function and the assembly of the basal membrane.

A specific inhibitor substance of the invention is capable of preventing or inhibiting the formation of the basal membrane and/or is specifically interfering with the assembly process of the basal membrane. Preferably, the specific inhibitor substance is selected from the group consisting of antibodies against collagen IV, laminin, entactin, accessory substances for proper function, or the assembly of the basal membrane; Fe-chelating agents; inhibitors of amino acids hydroxylases, such as prolyl-4-hydroxylase, lysine-hydroxylase; 2-oxoglutarate competitors; antisense nucleotides or nucleotide analogs which are able to prevent or inhibit the expression of basal membrane building elements, and the like.

According to the invention, there can further be used those inhibitor substances which are selected from the group consisting of N-oxaloglycine; Zn salts; pyridine derivatives, such as 5-arylcarbonyamino- or 5-arylcarbamoyl-derivatives, 2-carboxylate, 2,5 dicarboxylate, their ethyl esters or ethyl amides or -5-acyl sulfonamides, 2,4 dicarboxylate, their ethyl esters or ethylamides, or dimethoxyethylamides; 3,4 bipyridine, such as 5-amino-6-(1H)-one, 1,6-dihydro-2-methyl-6-oxo-5-carbonitril; 2,2'-bipyridine, such as 5,5'-dicarboxylic acid or its pharmaceutically acceptable salts, 4,4'-dicarboxylic acid ethyl ester or ethyl amide; 3,4'-dihydroxybenzoate, such as the diethyl ester; proline and its structural and functional analoges; beta-aminopropionitrile; desferrioxamine; anthracyclines; 2,7,8-trihydroxy anthraquinones, fibrostatin-C; coumalic acid or its pharmaceutically acceptable salts; 5-oxaproline, beta-lactam antibiotics.

In a preferred embodiment of the present invention the specific inhibitor substance(s) are applied in combination with one or more substances being capable of stimulating neuronal growth or inducing the expression of growth promoting proteins. Such neuronal growth stimulating substances are neurotrophic growth factors of the neurotrophin family and other growth factor families such as fibroblast growth factors, insulin and insulin-like growth factors, as well as epidermal growth factor, ciliary neuronotrophic growth factor (CNTF), glial cell-derived growth factor (GDNF), cytokines, neurotrophic proteoglycans and glycosamino-glycans, neural cell adhesion molecules like L1 (NILE), growth-associated proteins like GAP43 and anti-apoptotic proteins like bcl-2.

According to the invention it is preferred to locally apply the specific inhibitor substances in the neuronal tissue, intraventricularly, or systemically, in particular orally or intravenously.

The concentration of the specific inhibitor substance varies in view of the chemical nature. For example, antisense inhibitor substances may have more specific effects so that lesser amounts can be applied.

Typically, the specific inhibitor substance is applied in therapeutically effective amounts, such as 1 ng/kg to 1 mg/kg body weight, when low molecular compounds such as bipyridyl-derivatives are applied.

The invention also provides a medicament for the improvement of neuronal regeneration comprising a therapeutically effective amount of a specific inhibitor substance which is capable of prevention or inhibition of basal membrane formation induced by a lesion of neuronal tissue. Appropriate specific inhibitor substances are described hereinabove. The medicament may further comprise carrier substances or adjuvants in order to facilitate an appropriate application. The medicament may further comprise substances which are capable of stimulating neuronal growth.

The specific inhibitor substances which are capable of prevention or inhibition of basal membrane formation induced by a lesion of neuronal tissue can be used for the manufacturing of a medicament of the invention.

FIG. 1:

Expression of collagen IV and axonal sprouting after transection of the postcommissural fornix in untreated animals (b–d) and after injection of anti-Coll IV (e) or DPY (f) at two weeks postsurgery a, Sagittal view of the adult rat brain showing the course of the fornix and the location of the transection site. Marked deposition of collagen IV in the lesion site (arrow) and proximal stump (P) of an untreated animal at low (b) and high magnification (c). Note, the fine structure and the spatial orientation of collagen IV deposits perpendicular to the trajectory of the tract. d, In untreated animals regrowing fornix axons stop sharply at the lesion site (arrow). Collagen IV deposition is markedly reduced in the lesion site after anti-Coll IV (e) or DPY injection (f). Scale bars, 100 µm.

Figure 2:
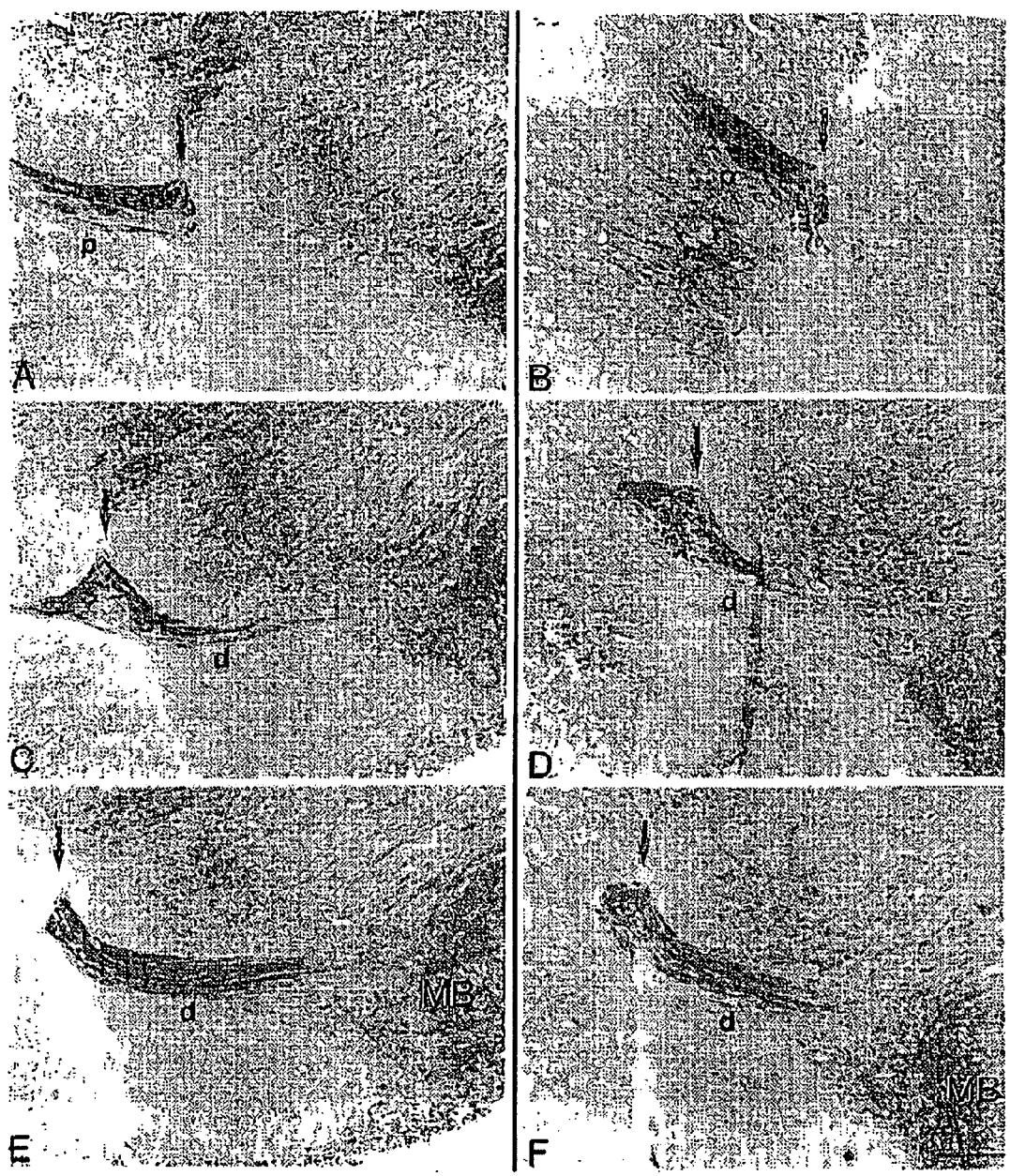

FIG. 2: Regeneration of transected fornix fibers across the lesion site in rats treated with anti-Coll IV (a, c, e) or DPY (b, d, f) at 6 weeks postsurgery. Sagittal serial sections reacted for NF-immunohistochemistry show that in both experimental groups fibers traverse the former lesion site (arrows) (c, d) and elongate within the distal stump (e, f) up to the mammillary body (MB). Scale bars, 100 µm.

Figure 3:
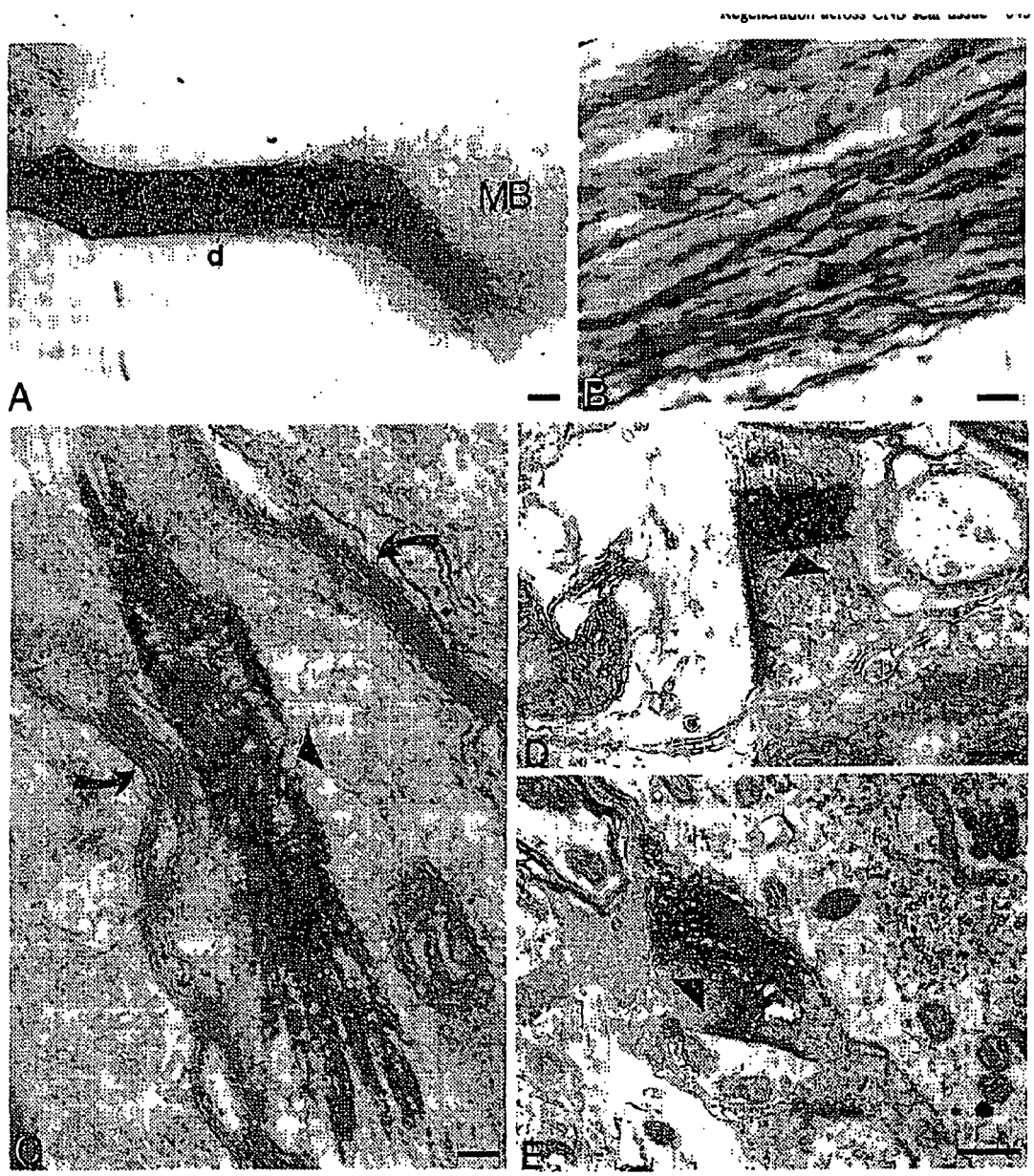

FIG. 3: Recovery of structural features of the regenerating fornix tract. a, b Anterograde tracing with biocytin of an anti-Coll IV treated animal at 6 weeks postsurgery reveals the large-number of regenerating axons (a), their elongation within the former pathway (a) and their fine varicose morphology (b). c, Large WGA-HRP-filled axon (arrowhead) in the mammillary body surrounded by compact myelin (arrows). d, e Electron micrographs of anterogradely WGA-HRP-labeled presynaptid terminals (arrow-heads) in the mammillary body at 6 weeks after anti-Coll IV, treatment. Scale bars, 100 µm (a), 50 µm (b), 0.1 µm (c), 0.5 µm (d), 1 µm (e).

Figure 4:
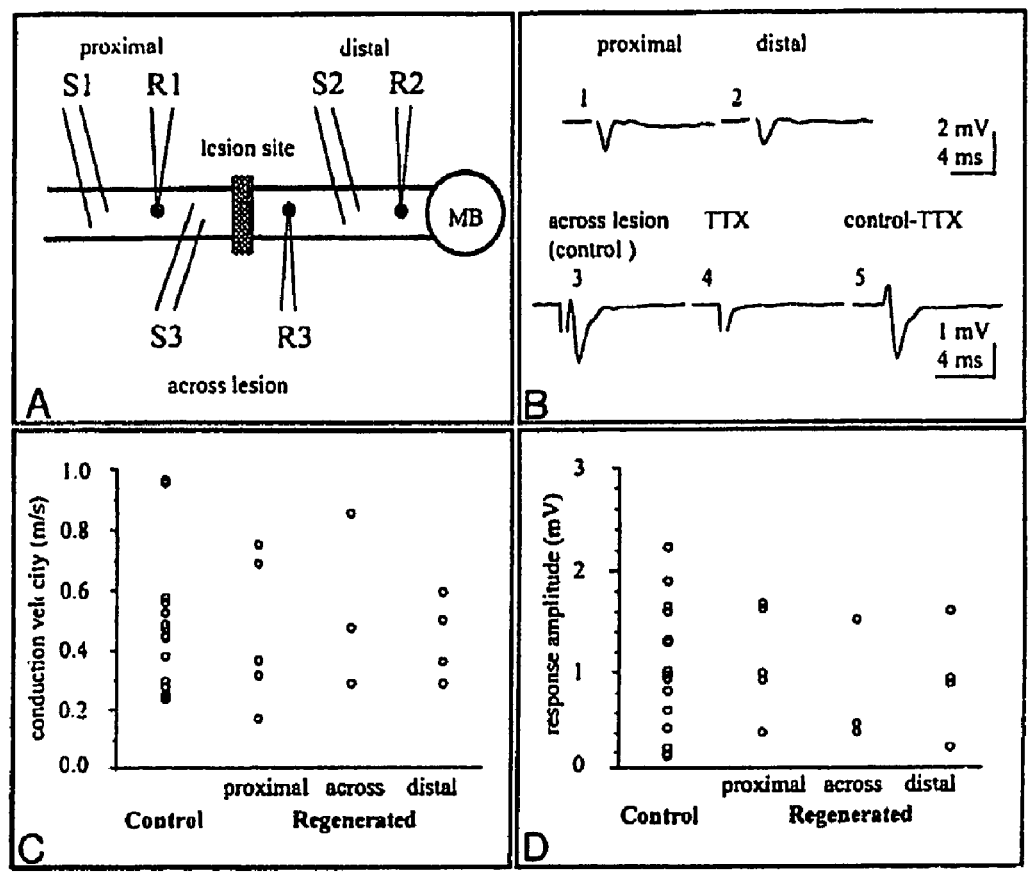

FIG. 4: Electrophysiological properties of fornix fibers in unlesioned rats and lesioned/injected animals with regeneration. a, Schematic illustration showing the location of the stimulating (S) and recording (R) electrode at various conditions. b, Characteristic recordings of extracellular action potentials in a sagittal slice prepared from an animal with regeneration. Recordings were obtained under conditions as illustrated in a Application of Tetrodotoxin (TTX) blocks the stimulus-evoked response. The net action potential is shown in trace 5. c and d, Distribution of conduction velocity and action potential response amplitude in unlesioned and lesioned/injected animals with regeneration.

The mechanically transected postcommissural fornix of the adult rat, a unidirectional and well-characterized fiber tract (8,9), was used to determine whether specific biochemical or immunochemical modulation of BM formation would provide a means to stimulate axon regeneration. Here we report that lesion-induced BM deposition can be significantly reduced by local injection of anti-collagen IV antibodies or alpha, alpha dipyridyl, an inhibitor of collagen triple helix formation and synthesis. Reducing the collagen network allowed massive axon elongation across the lesion site. The regenerating fornix fibers followed the original pathway, reinnervated their appropriate target, the mammillary body, were remyelinated and attained nearly normal conduction properties. On failure of adult mammalian CNS axons, we examined it's the spatio-temporal distribution pattern after penetrant CNS lesion and determined whether remodelling allows structural and functional regeneration of a transected CNS fiber tract.

The left postcommissural fornix was stereotactically transected in adult Wistar rats FIG. 1a) and the postlesion deposition of BM was analyzed using antibodies against collagen IV (Coll IV) and laminin (LN), the major and unique components of BM (10,11). By the end of the second week after lesion the center of the wound was filled by Coll IV- and LN-rich BM (FIG. 1b, c). These newly formed BM were either arranged in long continuous layers or associated with numerous blood vessels. Within the center of the wound the BM layers formed a parallel array aligned. perpendicular to the course of the fiber tract (FIG. 1b, c). In the vicinity of the transected stumps, however, BM layers were deposited as hook-like turns extending along the longitudinal tract axis for about 200 µm into the fornix stumps (FIG. 1c). In parallel with the deposition of the BM, sprouting axons in the proximal stump reached the lesion site. They failed to cross or bypass it but stopped growing at the wound border at about 2 weeks after lesion (FIG. 1d). The spatio-temporal coincidence of BM formation with the abrupt axonal growth arrest at the tract-lesion border strongly suggests that the newly formed perpendicular layers of BM could be a physical impediment for regenerating axons.

In an effort to modulate postlesion BM deposition, either polyclonal antibodies against collagen IV (anti-Coll IV; n=14) or the iron chelator a, a'-dipyridyl (DPY; n=9) were injected locally into the lesion center immediately after transection. DPY is a competitive inhibitor of prolyl 4-hydroxylase (12) and has been shown to prevent collagen triple helix formation (12), which results in feedback inhibition of procollagen synthesis. (13) and enhanced procollagen degradation (14). Control animals received a PBS injection (n=9) or were sham operated (n=3). Basal membrane formation was studied in response to antibody and drug treatment using immunohistochemical methods. Animals receiving a single injection of anti-Coll IV (80–160 ng) or DPY (1.6–16 µmol) showed a massive and specific reduction in Coll-immunopositive laminae and blood vessels in the lesion center and the fornix stumps at all examined survival time points. At 2 weeks after lesion+injection only a very small number of Coll-immunreactive structures perpendicular to the tract course had developed (FIG. 1e, f). Control animals, however, exhibited dense BM deposition as previously described for lesion only animals. The applied substances reduced the deposition of BM at the lesion site but did not affect the number or the distribution of vascular BM in the surrounding neuropil. Therefore, we conclude that the lesion-induced BM formation can be specifically reduced by immediate application of either anti-Coll IV antibodies or DPY.

To determine whether reduction of BM deposition would permit regeneration of transected axons across the lesion site, we studied the elongation of fornix axons after anti-ColI IV or DPY treatment using immunocytochemical staining. While sprouting fornix fibers in control animals ceased growing at the proximal stump-lesion interface (FIG. 1d) large numbers of axons entered and traversed the lesion center between 2 and 4 weeks after lesion+injection in those animals receiving anti-ColI IV (n=11) (FIG. 2a, c, e) or DPY treatment (n=6) (FIG. 2b, d, f). Most regenerating axons formed a loop over the lesion site, entered the distal stump and continued in a parallel bundle of fine and beaded axons within their previous pathway (FIG. 3a, b). They reached their appropriate target, the mammillary body, at about 4–6 weeks postsurgery. Anterograde tracing with WGA-HRP into the subiculum, the origin of the fornix (not shown), or biocytin application into the proximal fornix stump (FIG. 3a) provided proof, that the vast majority of fibers emerge from the formerly transected fornix tract. All regenerating fornix axons remained within their original pathway and did not invade the surrounding neuropil. The present results demonstrate that the failure of postcommissural fornix regeneration in rat brain, in fact, depends upon the formation of an axon growth-inhibiting BM at the lesion site that is oriented perpendicular to the tract course. Reduction of BM deposition seems to be a prerequisite but also a sufficient condition for the transected axons to regenerate across the lesion site.

Further preferred embodiments for restitution of functional circuitry after traumatic CNS lesion are the remyelination of regenerated fibers, the re-establishment of synaptic connections with the appropriate target and the restoration of normal conduction properties. Structural and functional properties of the regenerating axons were investigated using immunohistochemical, morphological and electrophysiological methods. Immunohistochemistry with an antibody against myelin basic protein demonstrated the remyelination of regenerated fornix axons along their entire length as early as 4 weeks after surgery (data not shown). This observation was confirmed by ultrastructural analysis of anterogradely WGA-HRP labeled axons in the distal stump which showed clear evidence of compact myelin sheath formation (FIG. 3c). In addition, ultrastructural studies provided evidence for the reestablishment of synaptic connections of regenerating axons within the mammillary body. Tracer reaction product was identified in presynaptic profiles with round vesicles that formed asymmetric synaptic junctions at unlabeled dendrites (FIG. 3d, e). The ultrastructural features of the labeled presynaptic profiles correspond to those described for the RA-type (round, asymmetric) of synaptic terminal, which is considered to be of subicular origin (8). The electrophysiological properties of regenerated fibers were studied using extracellular in vitro recording techniques applied to sagittal brain slices (400 mu m) of 8 unlesioned rats and 4 treated animals showing regenerated fiber tracts. In unlesioned animals electrical stimulation of the fornix fibers elicited an extracellular action potential with an amplitude of 1.02+/−0.14 mV and a conduction velocity of 0.48+/−0.05 m/s (mean +/−SEM, n=16, FIG. 4b–d). This axonal conduction velocity corresponds well to previously reported measurements (about 0.5 m/s for hippocampal Schaffer collaterals (15). Similar values for action potential amplitude and conduction velocity (1.12+/−0.21 mV, 0.46+/−0.1 m/s, n=5) were obtained in axon-regenerating animals when the stimulating (5) and the recording (R) electrodes were positioned proximally to the lesion site (see Si and Ri in FIG. 4a). In the latter animals, functionally intact fibers showing normal extracellular action potential amplitude and conduction velocity could also be demonstrated across (S3 and R3 in FIG. 4a; 0.8+/−0.29 mV, 0.54+/−0.14 m/s, n=3) and distal to the lesion site (S2 and R2 in FIG. 4a; 0.91+/−0.24 mV, 0.43+/−0.06 m/s, n=4) (FIG. 4c, d). In all animals, the stimulus-evoked extracellular responses were blocked by Tetrodotoxin, confirming their nature as Na+-dependent action potentials (FIG. 4b). From these data we conclude that the reorganization of the fornix tract is accompanied by structural and functional recovery of the regenerated axons.

Our results demonstrate that structural and functional restoration of lesioned mature fornix pathway can be achieved by reduction of BM formation in the lesion site. Data described here underscore the importance of extrinsic determinants in axonal regeneration but also demonstrates that once the axons have crossed the lesion scar other potential extrinsic regeneration constraints, like CNS myelin and oligodendrocytes (9,16–18) dense astrogliosis (6) and sulfated proteoglycans (19,20), do not impede their progress. The results further indicate that similar to other CNS circuits (21,22), fornix axons have an innate potential for regeneration and self-organization. These results give rise to new and promising concepts for therapeutic strategies that might contribute to the reduction of neurological deficits after CNS lesions.

The following examples are intended for further illustration of the invention but are not limiting.

Surgery. The left postcommissural fornix of 42 Wistar rats (180–210 g) was transected stereotactically at a distance of about 1 mm proximal to the target, the mammillary body, using a Scouten wire knife as described previously (9). The completeness of transection was confirmed by serial reconstruction of the lesion site for each of the animals. Immediately after transection animals received a topical application (1.6 µl) of either polyclonal antibodies against collagen, IV (anti-ColI IV, Biogenex, 50–100 µg/ml, n=14) or the iron chelator a, a'-dipyridyl (DPY, 1–10 mM, n=9). Substances were pressure injected (injection time 10 min) directly into the lesion site via a micropipette coupled to a microsyringe. Controls received equal amounts of phosphate-buffered saline (n=9) or sham operation (n=3).

Anterograde tracing was performed for analysis of fiber-course, ultrastructural morphology and target reinnervation. After a survival time of 6 weeks, anti-ColI IV-treated animals (n=4) received two injections of a 2% (w/v) solution of wheat-germ-agglutinin-HRP (WGA-HRP) into the left subicular complex (dorsal and caudal pole). Rats were perfused 3 days later with 2% paraformaldehyde and 2% glutaraldehyde in 0.1M phosphate buffer. Vibratome sections were reacted for WGA-HRP using tetramethylbenzidine as substrate (23).

Electron microscopy. For ultrastructural analysis vibratome sections of anti-ColI IV-treated animals were reacted for WGA-HRP, immersed for 12h in 1% osmium tetroxide and embedded in epon. Ultrathin sections were examined using a Hitachi H600 electron microscope.

Immunohistochemical staining. After a survival time of 4 days (d), 6 d, 2 weeks (w), 4 w and 6 w after surgery brains were removed, frozen in isopentan (−50/−60° C.) and cut into serial sagittal 10 µm thick sections. Sections were fixed with acetone (−20° C.), preincubated in 3% H2O2 (v/v) in methanol to block endogenous peroxidase, followed by PBS containing 3% (v/v) normal horse or normal goat serum to reduce unspecific staining and then incubated with one of the following primary antibodies: polyclonal anti-collagen IV (anti-ColI IV, Biogenex, 1:3), polyclonal anti-laminin (anti-LN, Biogenex, 1:5) or monoclonal cocktail against phosphorylated neurofilaments (anti-NF, Affinity, 1:800).

Following, avidin-biotin-peroxidase complex staining (Vector Labs) was done using standard procedures. For evaluation of remyelination brains were fixed with 4% paraformaldehyde, paraffinized, cut into 3-μm thick serial sagittal sections, deparaffinized and incubated as described above with a polyclonal anti-myelin basic protein (anti-MBP, Biogenex, 1:2) or anti-NF as primary antibodies. Specificity of the stainings was confirmed by omission of the primary antibody.

Electrophysiology and biocytin injections. Sagittal slices of 400 μm thickness were cut on a vibratome and maintained at 34–35°C. in an interface-type recording chamber. Artificial cerebrospinal fluid (ACSF) consisted of (in mM) 124 NaCl, 3 KCl, 1.25 NaH2PO4, 1.8 MgSO4, 1.6 CaCl2, 26 NaHCO3 and 10 glucose with a pH of 7.4 when saturated with 95% $O_2$–5% $CO_2$. Stimuli of 100 μs, 5–20 V were delivered via a bipolar tungsten electrode. Extracellular action potentials were registered with a recording electrode (3–5 MW) located in the middle of the postcommissural fornix. Tetrodotoxin (TTX, Sigma) was applied locally in a concentration of 10 μM (dissolved in ACSF) with a broken micropipette placed on the slice surface near the recording site. Injections of a small biocytin (Sigma) crystal into the fornix were performed with a miniature needle. After an incubation period of 8–10 h in the interface chamber, slices were fixed in 4% paraformaldehyde, resectioned and reacted with ABC peroxidase reagent (Vector Labs).

1. Reier, P. J., Stensaas, L. J. & Guth, L. *Spinal cord reconstruction*, (eds Kao, C. C., Bunge, R. P. & Reier, P. J.) 163–196 (Raven Press, New York, 1983).
2. Clemente, C. D. *Regeneration in the nervous system* (ed Windle, W. F.) 147–161 (Charles C. Thomas, Springfield, Ill., 1955).
3. Schnell, L. & Schwab, M. E. *Eur. J. Neurosci* 5, 1156–1171 (1993).
4. Krüger, S., Sievers, J., Hansen, C., Sadler, M. & Berry,.M. *J. Comp. Neurol* 249, 103–116 (1986).
5. Berry, M., Carlile, J. & Hunter, A. *J. Neurocytol* 25, 147–170 (1996).
6. Stichel, C. C. & Müller, H. W. *J. Neurocytol* 23, 615–630 (1994).
7. Feringa, E. R., Kowalski, T. F. & Vahlsing, H. L. *Ann. Neurol* 8, 148–154 (1980)
8. Allen, G. V. & Hopkins, D. A. *J. Comp. Neurol* 275, 39–64 (1988).
9. Stichel, C. C., Wunderlich, G., Schwab, M. E. & Müller, H. W. *Europ. J. Neurosci* 7, 401–411 (1995).
10. Yurchenco, P. D. & Schittny, J. C. *FASEB. J.* 4, 1577–1590 (1996).
11. Timpl, R. & Brown, *J. Curr. Opin. Cell. Biol* 8, 618–624 (1996).
12. Kivirikko, K. L., Myllyla, R. & Pihlajaniemi, T. *FASEB. J* 3, 1609–1617 (1989).
13. Ikeda, H., Wu, G. Y. & Wu, C. H. *Hepatology* 15, 282–287 (1992).
14. Bienkowski, R. S. *J. Cell. Physiol* 121, 152–158 (1984).
15. Andersen, P., Silfvenius, H., Sundberg, S., Sveen, O. & Wigström, H. *Brain. Res* 144, 11–18 (1978).
16. McKerracher, L. et al. *Neuron* 13, 805–811 (1994).
17. Mukhopadhyay, G., Doherty, P., Walsh, F. S., Crocker, P. R. & Filbin, M. T. *Neuron* 13, 757–767 (1994).
18. Schwab, M. E. & Caroni, P. *J. Neurosci* 8, 2381–2393 (1988).
19. Snow, A. D., Lemmon, V., Carrino, D. A., Caplan, A. I. & Silver, *J. Exp. Neurol* 109, 111–130 (1990).
20. Lips, K., Stichel, C. C. & Müller, H. W. *J. Neurocytol* 24, 449–464 (1995).
21. Iwashita, Y., Kawaguchi, S. & Murata, M. *Nature* 367, 167–170 (1994).
22. Kalderon, N. & Fuks, Z. *Proc. Natl. Acad. Sci* 93, 11179–11184 (1996).
23. Olucha, F., Martinez-Garcia, F. & Lopez-Garcia, C. *J. Neurosci. Meth* 13, 131–138 (1985).
24. Puchala, E. & Windle, W. F., *Exp. Neurol.* 55, 1–42 (1977).
25. Guth, L., Albuquerque, E. X., Deshpande, S. S., Barret, C. P., Donati, E. J. & Warnick, J. E., *J. Neurosurg.* 52, 73–86 (1980).

The invention claimed is:

1. A method of enhancing axonal regeneration comprising specific inhibition of basal membrane formation induced by a lesion of neuronal tissue in the spinal cord by local administration of an inhibitor of basal membrane formation to enhance axonal regeneration, wherein the inhibitor is an anti-collagen IV antibody, α,α,'-dipyridyl, 5,5'-dicarboxylic acid derivative of 2,2'-bipyridine, or desferrioxamine.

2. The method according to claim 1, wherein the inhibitor is administered in combination with a substance that stimulates neuronal growth.

3. The method according to claim 1, wherein the inhibitor is locally administered, intraventricularly, to the neuronal tissue.

4. The method according to claim 1, wherein the inhibitor is administered in an amount of 1 ng/kg to 1 mg/kg body weight.

5. A method of enhancing axonal regeneration comprising specific inhibition of basal membrane formation induced by a lesion of neuronal tissue in the post commissural fornix by local administration of an inhibitor of basal membrane formation to enhance axonal regeneration, wherein the inhibitor substance is an anti-collagen IV antibody, α,α,'-dipyridyl, 5,5'-dicarboxylic acid derivative of 2,2'-bipyridine, or desferrioxamine.

6. The method according to claim 5, wherein the inhibitor is administered in combination with a substance that stimulates neuronal growth.

7. The method according to claim 5, wherein the inhibitor is locally administered, intraventricularly, to the neuronal tissue.

8. The method according claim 5, wherein the inhibitor is administered in an amount of 1 ng/kg to 1 mg/kg body weight.

9. A method of treating a lesioned post commissural fornix, in which the lesion induces basal membrane formation, comprising locally administering an inhibitor substance to a body in need thereof and, thereby, treating the lesioned post commissural fornix, wherein the inhibitor substance is an anti-collagen IV antibody, α,α,'-dipyridyl, 5,5'-dicarboxylic acid derivative of 2,2'-bipyridine, or desferrioxamine.

10. The method according to claim 9, wherein the inhibitor is administered in combination with a substance that stimulates neuronal growth.

11. The method according to claim 9, wherein the inhibitor is locally administered, intraventricularly, to the neuronal tissue.

12. The method according to claim 9, wherein the inhibitor is administered in an amount of 1 ng/kg to 1 mg/kg body weight.

13. A method of treating a lesioned spinal cord, in which the lesion induces basal membrane formation, comprising locally administering an inhibitor substance to a body in need thereof and, thereby, treating the lesioned spinal cord, wherein the inhibitor substance treats the lesioned post commissural fornix or and is an anti-collagen IV antibody, α,α,'-dipyridyl, 5,5'-dicaboxylic acid derivative of 2,2'-bipyridine, or desferrioxamine.

14. The method according to claim 13, wherein the inhibitor is administered in combination with a substance that stimulates neuronal growth.

15. The method according to claim 13, wherein the inhibitor is locally administered, intraventricularly, to the neuronal tissue.

16. The method according to claim 13, wherein the inhibitor is administered in an amount of 1 ng/kg to 1 mg/kg body weight.

* * * * *